US00PP22237P2

(12) United States Plant Patent
Tsukahara

(10) Patent No.: US PP22,237 P2
(45) Date of Patent: Nov. 8, 2011

(54) ***PETUNIA* PLANT NAMED 'BLUETTE GRADATION PINK'**

(50) Latin Name: ***Petunia* hybrid**
Varietal Denomination: Bluette Gradation Pink

(75) Inventor: Jun Tsukahara, Yame (JP)

(73) Assignee: Daiichi Engei Co. Ltd.

( * ) Notice: Subject to any disclaimer, the term of this patent is extended or adjusted under 35 U.S.C. 154(b) by 70 days.

(21) Appl. No.: 12/660,102

(22) Filed: Feb. 18, 2010

(51) Int. Cl.
*A01H 5/00* (2006.01)

(52) U.S. Cl. ..... Plt./356.22

(58) Field of Classification Search ..... Plt./356.22
See application file for complete search history.

*Primary Examiner* — Kent L Bell

(57) ABSTRACT

A new and distinct *Petunia* cultivar named 'Bluette Gradation Pink' is disclosed, characterized by unique pink flowers with white throat and veins and a trailing plant habit. The new variety is a *Petunia*, suitable as an outdoor garden or container plant.

1 Drawing Sheet

Figure 1:
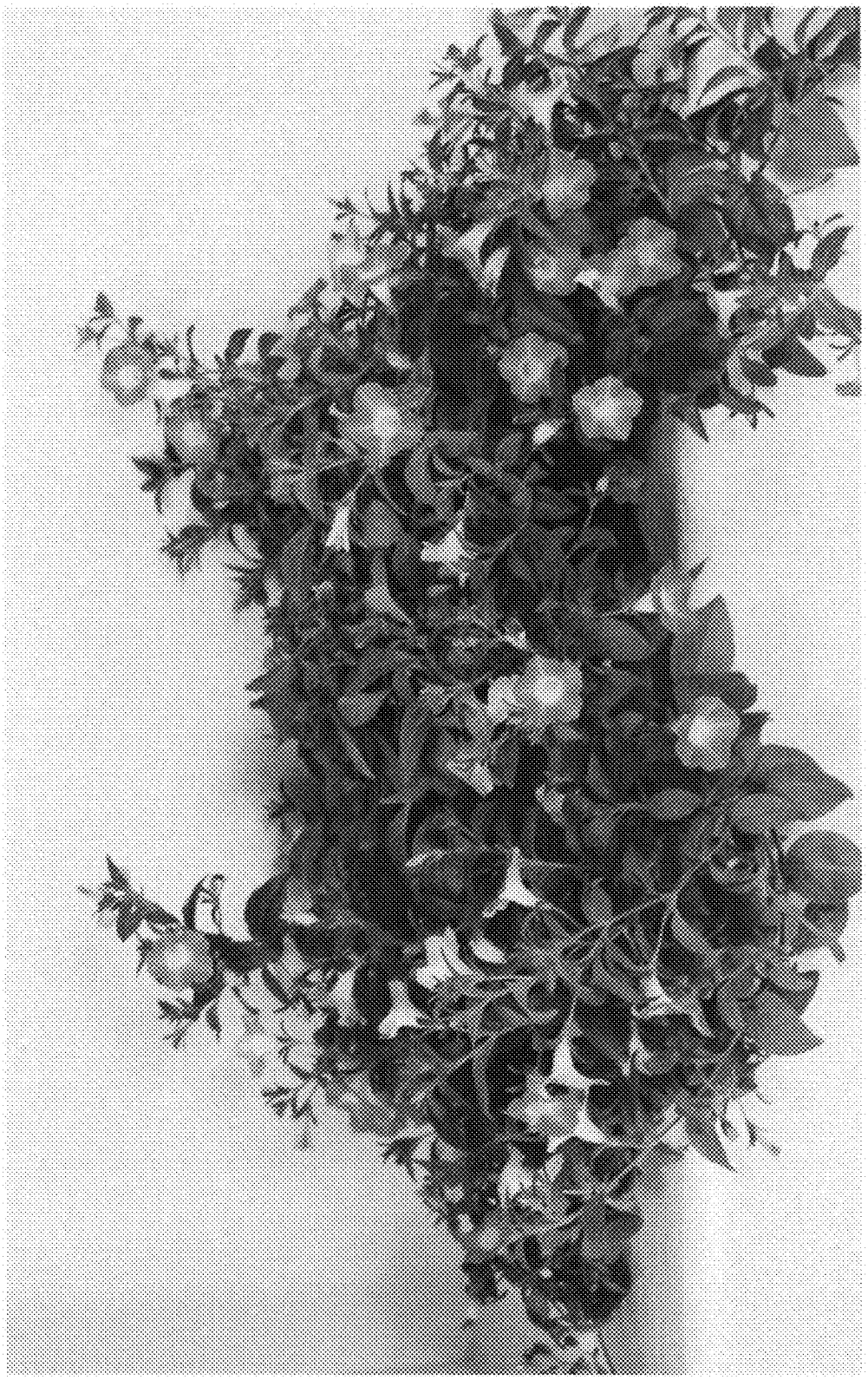

Latin name of the genus and species: *Petunia* hybrid.

Variety denomination: 'Bluette Gradation Pink'.

The new *Petunia* cultivar resulted as part of a planned breeding program by the inventor Jun Tsukahara, in Yame, Fukuoka, Japan. The objective of the breeding program was to develop new *Petunia* varieties with interesting colors and attractive plant forms.

The new variety resulted from the crossing of the seed parent, an unnamed, unpatented proprietary *Petunia* seedling with the pollen parent, an unnamed, unpatented proprietary *Petunia* seedling in September 2005. The new variety was discovered in November of 2007 by the inventor in a group of seedlings resulting from that crossing, in a commercial greenhouse in Yame, Fukuoka, Japan.

Asexual reproduction of the new cultivar 'Bluette Gradation Pink' was first performed by vegetative cuttings at a commercial greenhouse in Yame, Fukuoka, Japan in January 2008. Subsequently many generations have been produced and have shown that the unique features of this cultivar are stable and reproduced true to type.

SUMMARY OF THE INVENTION

The cultivar 'Bluette Gradation Pink' has not been observed under all possible environmental conditions. The phenotype may vary somewhat with variations in environment such as temperature, day length and light intensity, without however, any variance in genotype.

The following traits have been repeatedly observed and are determined to be the unique characeristics of 'Bluette Gradation Pink'. These characteristics in combination distinguish 'Bluette Gradation Pink' as a new and distinct *Petunia* cultivar:

1. Unique pink color with white veins and tube.
2. Trailing plant shape.

COMPARISON TO THE PARENT VARIETIES

Plants of the new cultivar 'Bluette Gradation Pink' are similar in most horticultural characteristics to plants of the unnamed proprietary seed parent. However, the seed parent has a larger overall flower size than the new cultivar. Additionally, the seed parent has thicker diameter stems than 'Bluette Gradation Pink'.

Plants of the new cultivar 'Bluette Gradation Pink' are similar in most horticultural characteristics to plants of the unnamed proprietary pollen parent. However, the pollen parent has darker colored flowers, and a smaller overall flower size than the new cultivar. Additionally, the pollen parent has thinner stems than the new cultivar.

COMPARISON TO COMMERCIAL VARIETIES

The new cultivar can be compared to the unpatented commercial variety 'Blue Duet Rose'. 'Bluette Gradation Pink' is similar to this commercial variety in most horticultural characteristics, especially plant habit, however, the new variety has flowers with a different colored throat and vein, whereas the comparison variety is all over one solid color.

BRIEF DESCRIPTION OF THE PHOTOGRAPH

The accompanying photograph in FIG. 1 illustrates in full color a typical plant of 'Bluette Gradation Pink' grown in a greenhouse, in a 6 inch pot. Age of the plant photographed is approximately 12 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurement describe 'Bluette Gradation Pink' plants grown in a commercial greenhouse in Oxnard, Calif. The growing temperature ranged from 18° C. to 25° C. The greenhouse is subject to partial shade. General light conditions are bright, normal sunlight with some shade during the brightest part of the day. Measurements and numerical values represent averages of typical plant types.

Botanical classification: *Petunia* hybrid 'Bluette Gradation Pink'

PROPAGATION

Time to initiate roots: About 7 days at approximately 25° C.
Time to develop roots: About 14 to 21 days at approximately 25° C.
Root description: Fine, fibrous.

PLANT

Growth habit: Trailing.
Age of the plant described: Approximately 12 weeks from a rooted cutting.
Pot size of plant described: Approximately 6 inch.
Height: Approximately 16 cm from soil line to top of plant.
Plant spread: Approximately 60 cm at widest point.
Growth rate: Rapid.
Branching characteristics: Free branching.
Length of primary lateral branches: Approximately 27 cm.
Quantity of primary lateral branches: Approximately 50
Characteristics of primary lateral branches:
*Diameter.*—Approximately 0.3 cm.
*Color.*—Near RHS Yellow-Green 144A.
*Texture.*—Pubescent.
*Strength.*—Highly flexible, moderately strong.
Internode length: Approximately 2.4 cm.

FOLIAGE

Leaf:
*Arrangement.*—Opposite.
*Quantity.*—Approximately 24 per main lateral branch.
*Average length.*—Approximately 4.5 cm.
*Average width.*—Approximately 2.5 cm.
*Shape of blade.*—Oblanceolate.
*Apex.*—Acute.
*Base.*—Obtuse.
*Margin.*—Entire.
*Texture of top surface.*—Matte with pubescence.
*Pubescence.*—Very short, less than 1 mm hairs, densely covering leaf.
*Aspect.*—Slightly recurved.
*Color.*—Young foliage upper side: Near RHS Green 137A. Young foliage under side: Near RHS Green 137C. Mature foliage upper side: Near RHS Green 137A. Mature foliage under side: Near RHS Green 137B.
*Venation.*—Type: Pinnate. Venation color upper side: Near RHS Yellow-Green 144B. Venation color under side: Near RHS Yellow-Green 144C.
*Petiole.*—Length: Approximately 0.3 cm. Diameter: Approximately 0.1 cm. Color: Near RHS Yellow-Green 144C. Texture: Pubescent.

FLOWER

Natural flowering season: Spring and Summer
Days to flowering from rooted cutting: Approximately 50.
Inflorescence and flower type and habit: Single salverform with fused petals.
Rate of flower opening: Approximately 2 to 3 days from bud to fully opened flower.
Flower longevity on plant: About 5 days.
Approximate quantity of flowers per plant: Approximately 200 flowers and buds.
Flowers persistent:
Bud:
*Shape.*—Ovate.
*Length.*—Approximately 1.4 cm.
*Diameter*—Approximately 1 cm.
*Color.*—Near RHS Red-purple 69D, flushed with RHS 71A near top.
Flower size:
*Diameter.*—Approximately 3.5 cm.
*Flower tube length.*—Approximately 2 cm.
*Flower tube diameter at distal end.*—Approximately 0.7 cm.
*Flower tube diameter at proximal end.*—Approximately 0.2 cm.
Petals:
*Length from throat.*—About 3.4 cm.
*Width.*—About 3.5 cm.
*Quantity.*—5, fused.
*Texture.*—Smooth.
*Apex.*—Truncate.
*Margin.*—Entire.
Color:
*When opening.*—Inner surface: Near RHS Red-Purple N74B. Outer surface: Near RHS Purple 75C.
*Fully opened.*—Inner surface: Near RHS Purple N78B. Outer surface: Near RHS Purple 77D. Flower throat (inside): Near RHS Green-White 157D. Flower throat, vein: Near RHS Yellow-Green 145B. Flower tube (outside): Near RHS White 155C. Flower tube, vein: Near RHS Yellow-Green 145B. Petal color, fading to: Near RHS Purple N78B.
Bud:
*Shape.*—Ovate.
*Length.*—Approximately 2.0 cm.
*Diameter.*—Approximately 0.5 cm.
*Color.*—Near RHS Yellow-Green 145C.
Calyx/sepals:
*Quantity per flower.*—5, fused at base.
*Shape.*—Oblong.
*Length.*—Approximately 2.1 cm.
*Width.*—Approximately 0.3 cm.
*Apex.*—Acute.
*Base.*—Fused.
*Margin.*—Entire.
*Texture.*—Pubescent.
*Color.*—Upper Surface: Near RHS Green 137A. Lower Surface: Near RHS Green 137C.
Peduncle:
*Length.*—Approximately 2.5 cm.
*Diameter.*—Approximately 0.2 cm.
*Color.*—Near RHS Green 143A.
*Orientation.*—Approximately 45 degree angle from stem. Slightly undulating.
Fragrance: Sweet.

REPRODUCTIVE ORGANS

Stamens:
*Number.*—5.
*Filament length.*—Approximately 1.4 cm.
Anthers:
*Length.*—Approximately 0.1 cm.
*Shape.*—Globular.

*Color.*—RHS Greyed-Orange 163C.

*Pollen.*—Not observed.

Pistil:

*Number.*—1.

*Length.*—Approximately 1.2 cm.

*Style.*—Length: Approximately 1 cm. Color: Near RHS White N155D.

*Stigma.*—Shape: Oblate. Color: Near RHS Yellow-Green 144B. Ovary Color: Near RHS Yellow-Green 144B.

OTHER CHARACTERISTICS

Seeds and fruits: Not observed.

Disease/pest resistance: Neither resistant nor susceptible to normal diseases and pests of *Petunia*.

Temperature tolerance: The new variety tolerates temperatures between approximately 6° to 35° C.

What is claimed is:

1. A new and distinct cultivar of *Petunia* plant named 'Bluette Gradation Pink' as herein illustrated and described.

* * * * *